United States Patent

Tokuyasu et al.

Patent Number: 5,994,520
Date of Patent: Nov. 30, 1999

[54] P-NITROPHENYL 2-ACETYLAMINO-4-O-(2-AMINO-2-DEOXY-β-D-GLUCOPYRANOSYL)-2-DEOXY-β-D-GLUCOPYRANOSIDE AND ITS SALTS, AND METHOD FOR PRODUCING THEM

[75] Inventors: Ken Tokuyasu; Hiroshi Ono, both of Tsukuba; Mayumi Kameyama, Abiko; Yutaka Mori; Shioka Hamamatsu, both of Tsukuba; Kiyoshi Hayashi, Tsuchiura, all of Japan

[73] Assignee: Director of National Food Research Institute, Ministry of Agriculture, Forestry and Fisheries, Tsukuba, Japan

[21] Appl. No.: 08/900,819

[22] Filed: Jul. 25, 1997

[30] Foreign Application Priority Data

May 30, 1997 [JP] Japan .................................. 9-156091

[51] Int. Cl.$^6$ .......................... C07H 15/04; C07H 15/10; C07H 15/00
[52] U.S. Cl. ...................... 536/17.4; 536/17.2; 536/18.5; 536/4.1; 536/179
[58] Field of Search ............................... 435/7.31, 72, 74, 435/100, 171; 536/17.2–17.4, 17.9

[56] References Cited

U.S. PATENT DOCUMENTS

| | | | |
|---|---|---|---|
| 5,219,749 | 6/1993 | Bouriotis et al. ........................ | 435/227 |
| 5,602,020 | 2/1997 | Laine et al. ............................. | 435/209 |

OTHER PUBLICATIONS

Matahira et al, N–Acetylglucosaminyl Disaccharide . . . , J. Carb. Chem., 14(2), pp. 214–217, 1995.

Tokuyasu et al., "Deacetylation of chitin oligosaccharides of dp 2–4 by chitin deacetylase from *Colletotrichum Lindemuthianum*", Carbohydrate Research 303 (1997) pp. 353–358.

Tokuyasu et al., "Purification and Characterization of Extracellular Chitin Deacetylase from *Colletotrichum Lindemuthianum*", Biosci. Biotech. Biochem. 60 (10), pp. 1598–1603 (1996).

Mitsutomi et al., "Action Pattern of *Aeromonas hydrophila* Chitinase on Partially N–Acetylated Chitosan", Agric. Biol. Chem. 54 (4), pp. 871–877 (1990).

K. Tokuyasu et al., "Preparation of Chitosan–related Compounds by Using Enzymatic Deacetylation Method", *Chitin and Chitosan Research*, 3, No. 2, pp. 142–143 (1997).

John et al., "Rhizobium NodB Protein Involved in Nodulation Signal Synthesis is a Chitooligosaccharide Deacetylase", Proc. Natl. Acad. Sci., 90, 625–629 (1993).

Primary Examiner—James O. Wilson
Assistant Examiner—Howard Owens
Attorney, Agent, or Firm—Frishauf, Holtz, Goodman, Langer & Chick, P.C.

[57] ABSTRACT

Disclosed is p-nitrophenyl 2-acetylamino-4-O-(2-amino-2-deoxy-β-D-glucopyranosyl)-2-deoxy-β-D-glucopyranoside of formula (1) and its acid-addition salts.

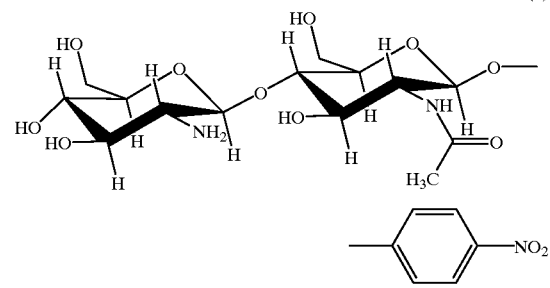

The compound of formula (1) is produced by reacting a p-nitrophenyl derivative of chitin dimer with a microorganism-derived deacetylase. The compound and its salts do not act on exo-type chitinases, and are specific to only endo-type ones.

17 Claims, 3 Drawing Sheets

P-NITROPHENYL 2-ACETYLAMINO-4-O-(2-AMINO-2-DEOXY-β-D-GLUCOPYRANOSYL)-2-DEOXY-β-D-GLUCOPYRANOSIDE AND ITS SALTS, AND METHOD FOR PRODUCING THEM

FIELD OF THE INVENTION

The present invention relates to p-nitrophenyl 2-acetylamino-4-O-(2-amino-2-deoxy-β-D-glucopyranosyl)-2-deoxy-β-D-glucopyranoside and its salts, and to a method for producing them. This substance does not react with exo-type chitinases, but reacts with endo-type chitinases to give color-indicating p-nitrophenol. As compared with commercially-available substrates, therefore, this substance can be a substrate for measurement of enzymatic activities having a higher specificity to the mode of decomposition of enzymes and having a higher sensitivity.

BACKGROUND OF THE INVENTION

Chitinases exist widely in bacteria, fungi, plants, arthropods and vertebrates, and various studies of chitinases have been being made for the purpose of clarifying the meanings of their existence in such organisms and for applying them to industrial use.

On the other hand, for determining the activities of chitinases, known are a turbidimetric method, a method of measuring viscosity, a method of utilizing radioactivity and a method of quantifying reducing sugars, all of which are problematic in that they take much time and are troublesome.

With the development of glyco-chain engineering, a method of using a monose derivative having a p-nitrophenyl group at its reducing terminal to measure enzymatic activities has been developed, in which the activities of enzymes, especially those of exo-type ones are measured rapidly. However, no effective method has as yet been developed for measuring the activities of endo-type enzymes.

P-nitrophenyl derivatives of chitin-oligosaccharides which have been considered to be usable for the measurement of the activities of endo-type enzymes are problematic in that they are also substrates for exo-type enzymes capable of decomposing oligosaccharides successively from their end. Therefore, the development of substrates having a high specificity to endo-type enzymes is desired.

In practice, to identify endo-type or exo-type enzymes, employed is a complicated method of determining the reduction in the viscosity of the reaction system comprising an enzyme being reacted with a substrate. In this method, the viscosity of the reaction system comprising an endo-type enzyme being reacted with a substrate is rapidly lowered, while that of the reaction system comprising an exo-type enzyme being reacted with a substrate is slowly lowered.

SUMMARY OF THE INVENTION

The object of the present invention is to solve the above-mentioned problems in the prior art, and to provide a compound capable of being a substrate that does not act on exo-type chitinases but is specific to endo-type ones, and also a method for producing it.

Specifically, the present invention provides p-nitrophenyl 2-acetylamino-4-O-(2-amino-2-deoxy-β-D-glucopyranosyl)-2-deoxy-β-D-glucopyranoside of the following formula (1) and its acid-addition salts.

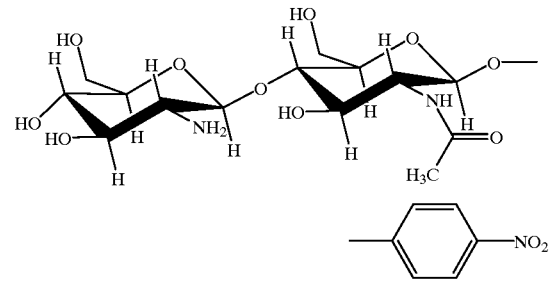

(1)

The present invention also provides a method for producing p-nitrophenyl 2-acetylamino 4-O-(2-amino-2-deoxy-β-D-glucopyranosyl)-2-deoxy-β-D-glucopyranoside of the above-mentioned formula (1) and its acid-addition salts, which comprises reacting a p-nitrophenyl derivative of a chitin dimer with a microorganisms-derived deacetylase.

In one preferred embodiment of the method of the invention, said p-nitrophenyl derivative of a chitin dimer is p-nitrophenyl-di-N-acetyl-β-D-chitobioside.

DETAILED DESCRIPTION OF THE PREFERRED EMBODIMENTS

Figure 1:
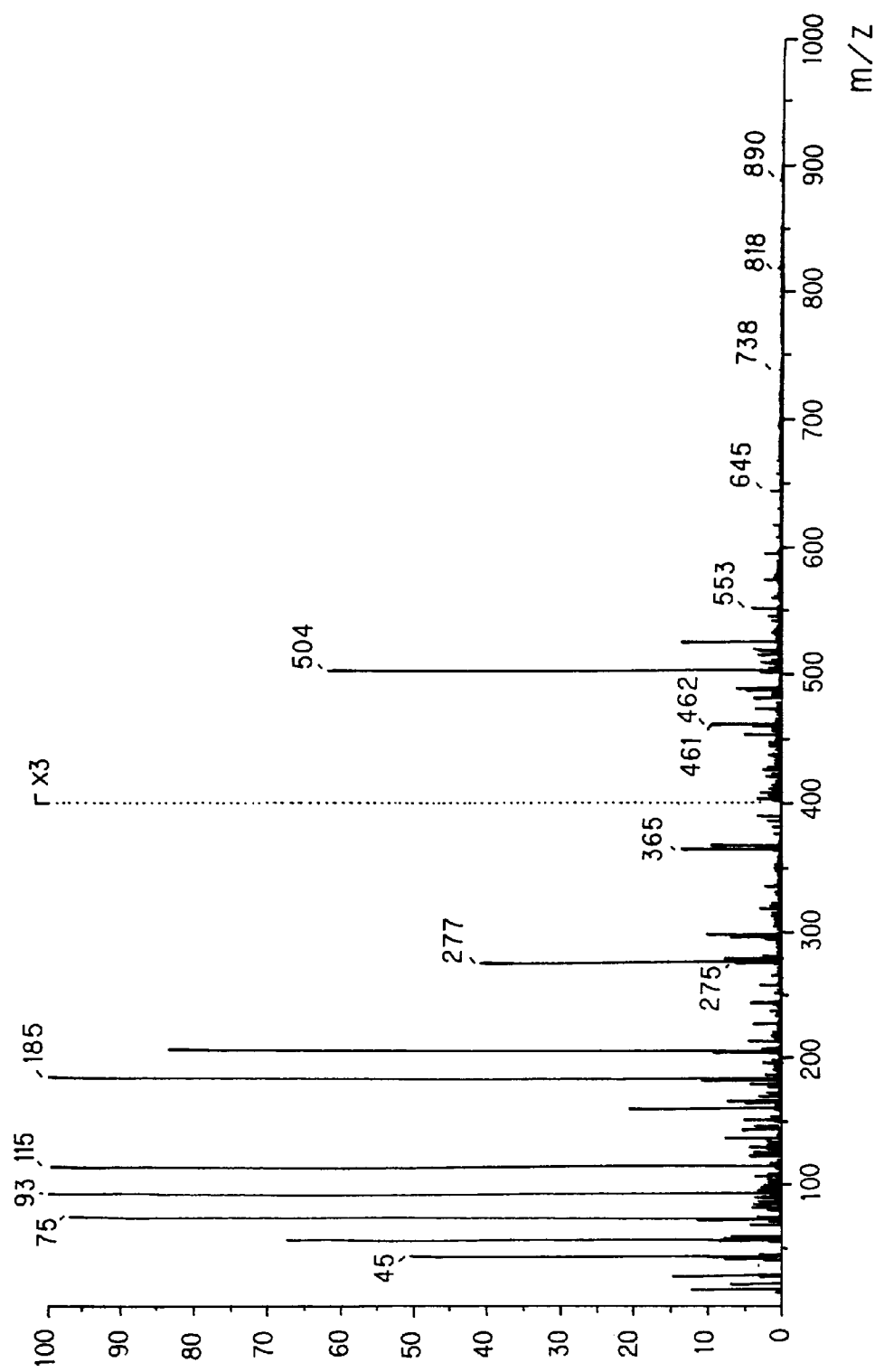
FIG. 1 is a mass spectrum of the compound of the invention.

Some glyco-chain derivatives having a p-nitrophenyl group are produced and sold in the market as substrates for measuring the activities of glycosidases, etc. However, the compound of the above-mentioned formula (1) of the present invention is not disclosed in literature and is a novel compound.

Salts of the compound of the invention may be acid-addition salts (expressed with HX in the formula), including, for example, hydrochlorides, acetates, etc. The salts may be represented by the following formula (2):

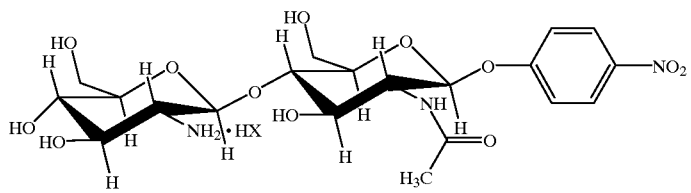

(2)

Now, the compound of the invention, p-nitrophenyl 2-acetylamino-4-O-(2-amino-2-deoxy-β-D-glucopyranosyl)-2-deoxy-β-D-glucopyranoside and its salts, and a method for producing them are referred to hereinunder.

The compound of the invention can be obtained by reacting a p-nitrophenyl derivative of a chitin dimer with a microorganisms-derived deacetylase.

As the p-nitrophenyl derivative of a chitin dimer, employable is any commercially-available one. For example, preferred is p-nitrophenyl-di-N-acetyl-β-D-chitobioside.

The microorganisms-derived deacetylase may be, for example, an imperfect fungi-derived chitin deacetylase, such as typically *Colletotrichum lindemuthianum* ATCC 56676-derived chitin deacetylase (see Biosci. Biotech. Biochem., 60 (10), 1598–1603, 1996).

This enzyme can be obtained, for example, as follows. The spores of the above-mentioned imperfect fungus are incubated in a liquid medium, and the active fraction is recovered from the culture. This can be directly used as a crude enzyme liquid, or may be purified in any ordinary manner to give a pure enzyme (see Japanese Patent Application Laid-Open No. 8-289785).

This enzyme is reacted with a raw material compound of the above-mentioned p-nitrophenyl derivative of a chitin dimer, whereby only the acetyl group of the N-acetylglucosamine residue at the non-reducing terminal of said derivative is removed to convert said residue to a glucosamine residue, thereby obtaining the intended p-nitrophenyl 2-acetylamino-4-O-(2-amino-2-deoxy-β-D-glucopyranosyl)-2-deoxy-β-D-glucopyranoside of the invention.

Concretely, a p-nitrophenyl derivative of a chitin dimer is dissolved in sodium tetraborate/HCl buffer (pH 8.5) to prepare a solution having a substrate concentration of from 0.1 to 0.5%, preferably about 0.2%.

To this solution is added from 0.01 to 0.3 units, preferably about 0.1 units of a microorganisms-derived chitin deacetylase, and reacted with said derivative at from 30 to 60° C., preferably at 45° C., for from 1 to 6 hours, preferably from 2 to 4 hours.

Next, the reaction product is adsorbed by a cation-exchange resin, and the non-reacted, raw material substance is removed. By elevating the pH value of the resin, the intended product is eluted. The cation-exchange resin to be used is preferably Amberlite CG-120 Column, CM-Sephadex or the like.

Next, the resulting eluate is applied into a reversed-phase column as equilibrated with water, and the adsorbed fraction is eluted with methanol, then de-salted and purified. The reversed-phase column to be used is preferably Sep-Pak plus C-18.

If desired, a suitable acid, such as hydrochloric acid, acetic acid or the like, may be added to the thus-obtained product to prepare its salt.

The structure of the substance obtained in the manner mentioned above was analyzed through mass-spectrometric and magnetic nucleic resonance analysis. This substance was not found in Chemical Abstracts (1957 to 1997). Therefore, it was decided that this substance is a novel compound.

This substance is essentially used as a substrate for measuring the activities of endo-type chitinases. As has been mentioned hereinabove for conventional color-indicating substrates for measuring the activities of chitinases, it is impossible to determine only the activities of exo-type chitinases existing in mixtures with endo-type ones if such conventional color-indicating substrates are used. As opposed to these, however, the novel compound of the present invention is not decomposed by any exo-type chitinases but is decomposed by only endo-type ones. Therefore, it is believed that the compound of the invention is helpful in providing a method for analyzing the mechanism of the decomposition of chitinases and in improving the efficiency in the determination of the activities of endo-type chitinases.

EXAMPLES

Now, the present invention is described in more detail with reference to the following Examples, which, however, are not intended to restrict the scope of the invention.

Example 1

(1) Purification of chitin deacetylase:

Imperfect fungus, *Colletotrichum lindemuthianum* ATCC 56676 was inoculated into a medium comprising 0.28% glucose, 0.123% magnesium sulfate (7-hydrate), 0.2% proteose peptone, 0.272% potassium dihydrogenphosphate and 2.0% agar, and statically cultivated in the dark at 25° C. for 7 days to produce black cells.

Next, the cells were implanted into 200 ml of a medium (pH 5.8) comprising 1% malt extract, 0.4% yeast extract and 0.4% glucose and put in a 500-ml Erlenmeyer flask, and incubated in the dark at 22° C. with shaking at a revolution of 100 rpm for one minute. Around the 8th day, the cells began to secrete a substance having an enzymatic activity in the culture, and the enzymatic activity increased until the 18th day. After 18 days, the incubation was stopped, and the culture was filtered through a nylon filter and then passed through glass fibers to remove fine grains to recover the culture filtrate.

Ammonium sulfate was added to the filtrate at 4° C. to have a concentration of 80% saturation, then left statically as it was overnight, and thereafter centrifuged to recover the precipitate. This precipitate was dissolved in a small amount of 50 mM sodium tetraborate/HCl buffer (pH 8.5) and dialyzed against the same buffer. The resulting dialysate, crude enzyme liquid was fractionated and purified through hydrophobic interaction chromatography and anion chromatography to obtain a chitin deacetylase. This enzyme gave a single band in SDS gel electrophoresis (see Japanese Patent Application Laid-Open No. 8-289785).

(2) Production of p-nitrophenyl 2-acetylamino-4-O-(2-amino-2-deoxy-β-D-glucopyranosyl)-2-deoxy-β-D-glucopyranoside:

0.40 mg of p-nitrophenyl-di-N-acetyl-β-D-chitobioside (manufactured by Seikagaku Kogyo KK) was dissolved in 0.2 ml of 20 mM sodium tetraborate/HCl buffer (pH 8.5), and 0.05 units of the imperfect fungus *Colletotrichum lindemuthianum*-derived, pure chitin deacetylase obtained in (1) was added thereto and reacted at 45° C. for 3 hours.

This reaction was repeated 6 times, and the reaction liquids were combined, and then passed through a cation-exchange resin column (Amberlite CG-120 Column, manufactured by Organo Co.) that had been equilibrated with HCl and then washed with water, whereby the reaction product was held by the resin. Next, 50 mM sodium tetraborate/HCl buffer (pH 8.5) was passed through the column to elute the product.

Next, the thus-eluted product was applied to a solid-phase extraction column (Sep-Pak plus C-18, manufactured by Waters Co.) that had been equilibrated with water, to be held by the solid phase, and thereafter eluted with 100% methanol.

The thus-purified compound was analyzed with a mass spectrometer (manufactured by JEOL Co.), which gave a signal of $[M+H^+]=504$. Thus, it was presumed that the compound obtained herein has a molecular weight of 503.

Figure 2:
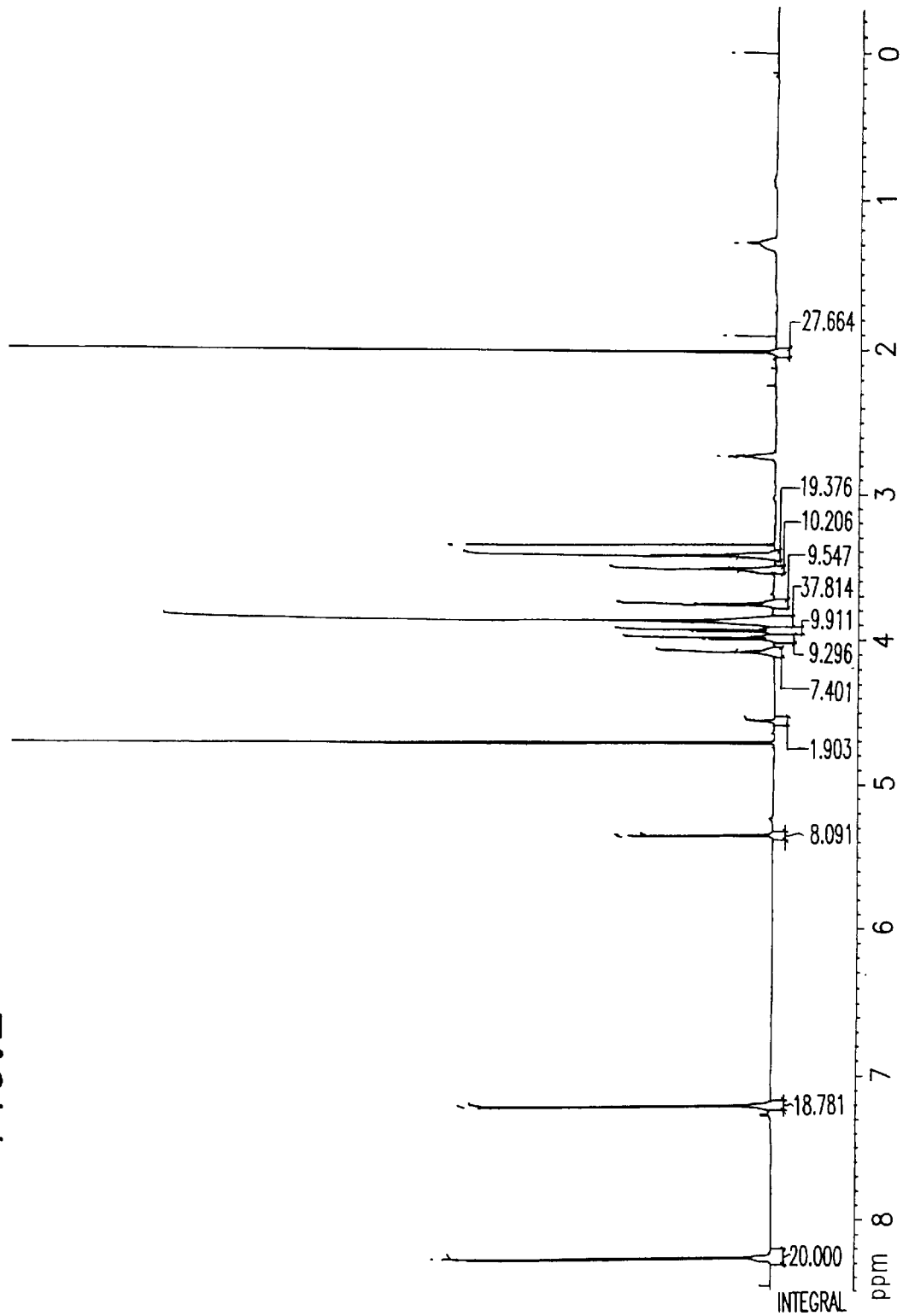
FIG. 2 is a $^1$H-NMR spectrum of the compound of the invention.

As a result of its $^1$H-NMR analysis, the compound was decided to have a structure of p-nitrophenyl 2-acetylamino-4-O-(2-amino-2-deoxy-β-D-glucopyranosyl)-2-deoxy-β-D-glucopyranoside. FIG. 1 is a mass spectrum of the compound obtained herein. FIG. 2 is a $^1$H-NMR spectrum of said compound.

Example 2

0.007 units of β-N-acetylhexosaminidase (derived from *Penicillum oxalicum*, manufactured by Seikagaku Kogyo KK) having an exo-type chitinase activity was reacted with 0.05% of the pure p-nitrophenyl 2-acetylamino-4-O-(2-amino-2-deoxy-β-D-glucopyranosyl)-2-deoxy-β-D-glucopyranoside obtained in Example 1, in 50 mM sodium citrate buffer (pH 4.5) at 37° C. for 1 hour.

0.01 ml of the reaction liquid was mixed 0.49 ml of 200 mM boric acid buffer (pH 8.6), and the yellowed p-nitrophenol was quantified by measuring its absorbance at 400 nm. For control, p-nitrophenyl derivative of N-acetylglucosamine was used as the substrate.

The amount of p-nitrophenol as liberated through the enzymatic reaction with the compound of the invention was only about 2%, as compared with that in the control using the same amount of p-nitrophenyl derivative of N-acetylglucosamine as the substrate.

Example 3

The pure p-nitrophenyl 2-acetylamino-4-O-(2-amino-2-deoxy-β-D-glucopyranosyl)-2-deoxy-β-D-glucopyranoside obtained in Example 1 was reacted and decomposed with 0.004 units of *Streptomyces griseus*-derived, endo-type chitinase (manufactured by Sigma Co.), in 20 mM sodium phosphate buffer at 37° C. for 1 hour.

Immediately after the start of the reaction, free p-nitrophenol was formed to yellow the reaction liquid.

Figure 3A:
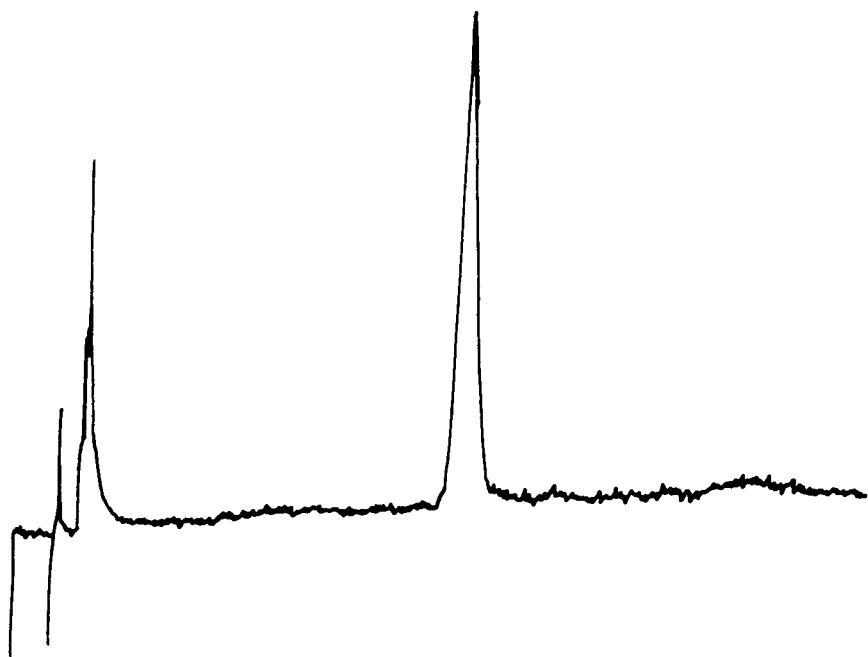
FIG. 3(A) is a chromatogram obtained as a result of high-performance liquid chromatography of a standard sample of 2-acetamido-2-deoxy-4-O-(2-amino-2-deoxy-β-D-glucopyranosyl)-D-glucose.

A sample of the reaction mixture was analyzed through high-performance liquid chromatography (using a column, CarboPac PA-1 manufactured by Dionex Co.; an eluent of 15 mM NaOH; and a pulsed amperometry detector), whereby the structure of the free sugar formed through the enzymatic reaction was determined. FIG. 3(A) is a chromatogram obtained as a result of high-performance liquid chromatography of a standard sample of 2-acetamido-2-deoxy-4-O-(2-amino-2-deoxy-β-D-glucopyranosyl)-D-glucose; and FIG. 3(B) is a chromatogram obtained as a result of high-performance liquid chromatography of the enzymatic decomposate of the compound of Example 1.

Figure 3B:
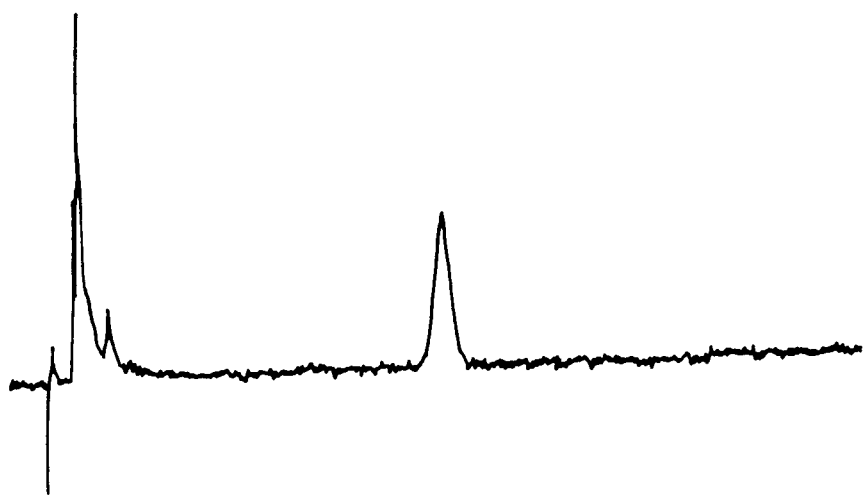
FIG. 3(B) is a chromatogram obtained as a result of high-performance liquid chromatography of a decomposate of the compound of the invention as decomposed with an endo-type chitinase.

As in these FIGS. 3(A) and 3(B), the retention time for the enzymatic decomposate, free sugar was the same as that for the standard sample of 2-acetamido-2-deoxy-4-O-(2-amino-2-deoxy-β-D-glucopyranosyl)-D-glucose, which verified that the compound of Example 1 was decomposed with the endo-type chitinase to give the free sugar, biose unit constituting said compound.

As has been mentioned in detail hereinabove with reference to its embodiments, the present invention provides a novel compound, p-nitrophenyl 2-acetylamino-4-O-(2-amino-2-deoxy-β-D-glucopyranosyl)-2-deoxy-β-D-glucopyranoside and its salts. The compound and its salts do not have any influence on exo-type enzymes, if any, in enzyme mixtures, and therefore can be used for rapidly measuring the activities of only endo-type chitinases in enzyme mixtures.

While the invention has been described in detail and with reference to specific embodiments thereof, it will be apparent to one skilled in the art that various changes and modifications can be made therein without departing from the spirit and scope thereof.

The entire disclosure of Japanese Patent Application No. 9-156091 filed on May 30, 1997 including specification, claims and summary are incorporated herein by reference in its entirety.

What is claimed is:

1. P-nitrophenyl 2-acetylamino-4-O-(2-amino- 2-deoxy-β-D-glucopyranosyl)-2-deoxy-β-D-glucopyranoside of the following formula (1) and hydrochloride and acetate salts thereof:

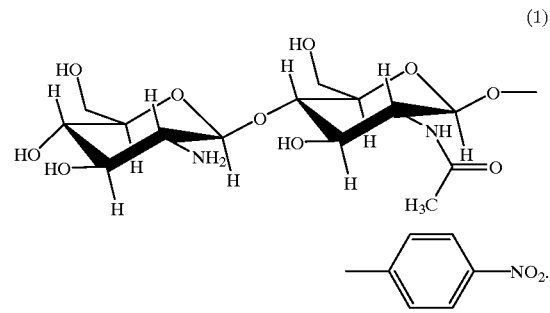

(1)

2. A method for producing p-nitrophenyl 2-acetylamino-4-O-(2-amino-2-deoxy-β-D-glucopyranosyl)-2-deoxy-β-D-glucopyranoside and said salts of claim 1, which comprises reacting a p-nitrophenyl compound of a chitin dimer with a *Colletotrichum lindemuthianum* derived deacetylase.

3. The method as claimed in claim 2, wherein said p-nitrophenyl compound of the chitin dimer is p-nitrophenyl-di-N-acetyl-β-D-chitobioside.

4. The method as claimed in claim 2, wherein the deacetylase is *Colletotrichum lindemuthianum* ATCC 56676-derived chitin deacetylase.

5. The method as claimed in claim 2, wherein the p-nitrophenyl compound of a chitin dimer is dissolved in sodium tetraborate/HCl buffer to prepare a solution having a substrate concentration of 0.1 to 5%.

6. The method as claimed in claim 2, wherein the *Colletotrichum lindemuthianum*-derived deacetylase is present in an amount of 0.01 to 0.3 units.

7. The method as claimed in claim 2, wherein the method is carried out at a temperature of 30 to 60° C. for 1 to 6 hours.

8. The method as claimed in claim 7, wherein the method is carried out for 1 to 6 hours.

9. The method as claimed in claim 8, wherein the method is carried out for 1 to 4 hours.

10. The method as claimed in claim 3, wherein the deacetylase is *Colletotrichum lindemuthianum* ATCC 56676-derived chitin deacetylase.

11. The method as claimed in claim 10, wherein the *Colletotrichum lindemuthianum* ATCC 56676-derived chitin deacetylase is present in an amount of 0.01 to 0.3 units.

12. The method as claimed in claim 11, wherein the method is carried out at a temperature of 30 to 60° C. for 1 to 6 hours.

13. The method as claimed in claim 12, wherein the method is carried out for 2 to 4 hours at a temperature of 45° C.

14. The method as claimed in claim 13, wherein the p-nitrophenyl-di-N-acetyl-β-D-chitobioside is dissolved in a sodium tetraborate/HCl buffer to prepare a solution having a substrate concentration of 0.1 to 0.5%.

15. The method as claimed in claim 14, wherein the substrate concentration is 0.2%.

16. The method as claimed in claim 15, wherein the *Colletotrichum lindemuthianum* ATCC-56676-derived chitin deacetylase is present in an amount of 0.1 units.

17. The hydrochloride salt of the p-nitrophenyl 2-acetylamino-4-O-(2-amino-2-deoxy-β-D-glucopyranosyl)-2-deoxy-β-D-glucopyranoside of claim 1.

* * * * *